(12) United States Patent
Hoffman et al.

(10) Patent No.: US 8,088,154 B2
(45) Date of Patent: Jan. 3, 2012

(54) MEDICAL DEVICE DELIVERY SYSTEM WITH SHEATH SEPARATION

(75) Inventors: Grant T Hoffman, Bloomington, IN (US); Brian C Case, Lake Villa, IL (US)

(73) Assignee: Cook Medical Technologies LLC, Bloomington, IN (US)

( * ) Notice: Subject to any disclaimer, the term of this patent is extended or adjusted under 35 U.S.C. 154(b) by 541 days.

(21) Appl. No.: 12/059,241

(22) Filed: Mar. 31, 2008

(65) Prior Publication Data

US 2008/0255580 A1   Oct. 16, 2008

Related U.S. Application Data

(60) Provisional application No. 60/909,450, filed on Mar. 31, 2007.

(51) Int. Cl.
*A61F 2/06* (2006.01)
(52) U.S. Cl. ..................................................... 623/1.11
(58) Field of Classification Search .................. 604/264; 606/108; 623/1.11–1.12, 1.23
See application file for complete search history.

(56) References Cited

U.S. PATENT DOCUMENTS

| | | | |
|---|---|---|---|
| 5,290,295 | A | 3/1994 | Querals |
| 5,755,769 | A | 5/1998 | Richard |
| 6,126,685 | A | 10/2000 | Lenker |
| 6,200,336 | B1 | 3/2001 | Pavcnik |
| 6,254,628 | B1 | 7/2001 | Wallace |
| 6,827,731 | B2 * | 12/2004 | Armstrong et al. .......... 623/1.12 |
| 2003/0032941 | A1 * | 2/2003 | Boyle et al. .................... 604/533 |
| 2003/0149467 | A1 * | 8/2003 | Linder et al. ................. 623/1.11 |
| 2004/0186558 | A1 | 9/2004 | Pavcnik |
| 2004/0260389 | A1 | 12/2004 | Case |
| 2006/0167417 | A1 | 7/2006 | Kratz |

FOREIGN PATENT DOCUMENTS

| | | |
|---|---|---|
| EP | 0391544 | 10/1990 |
| EP | 0391544 A1 | 10/1990 |
| WO | 0197715 | 12/2001 |
| WO | 0197715 A1 | 12/2001 |
| WO | 02060345 | 8/2002 |
| WO | 02060345 A2 | 8/2002 |

* cited by examiner

*Primary Examiner* — Ryan Severson
*Assistant Examiner* — Ashley Cronin
(74) *Attorney, Agent, or Firm* — Buchanan Nipper

(57) ABSTRACT

Medical device delivery systems and associated methods are provided. Delivery systems according to the invention include an elongated tubular member and a body member, such as a dilator, disposed therein. An intraluminal medical device is disposed on the dilator and within the tubular member prior to deployment. The delivery system includes a means for separating two or more portions of the distal end of the tubular member that aids in deploying the intraluminal medical device from the delivery system by separating two or more portions of the tubular member from each other to facilitate release of the intraluminal medical device from the body member. Various structures can be used for means for separating, including a cutting ring, activateable material on the tubular member, or other suitable structure. The provided devices and methods reduce friction occuring from relative movement between the sheath and dilator during deployment.

20 Claims, 7 Drawing Sheets

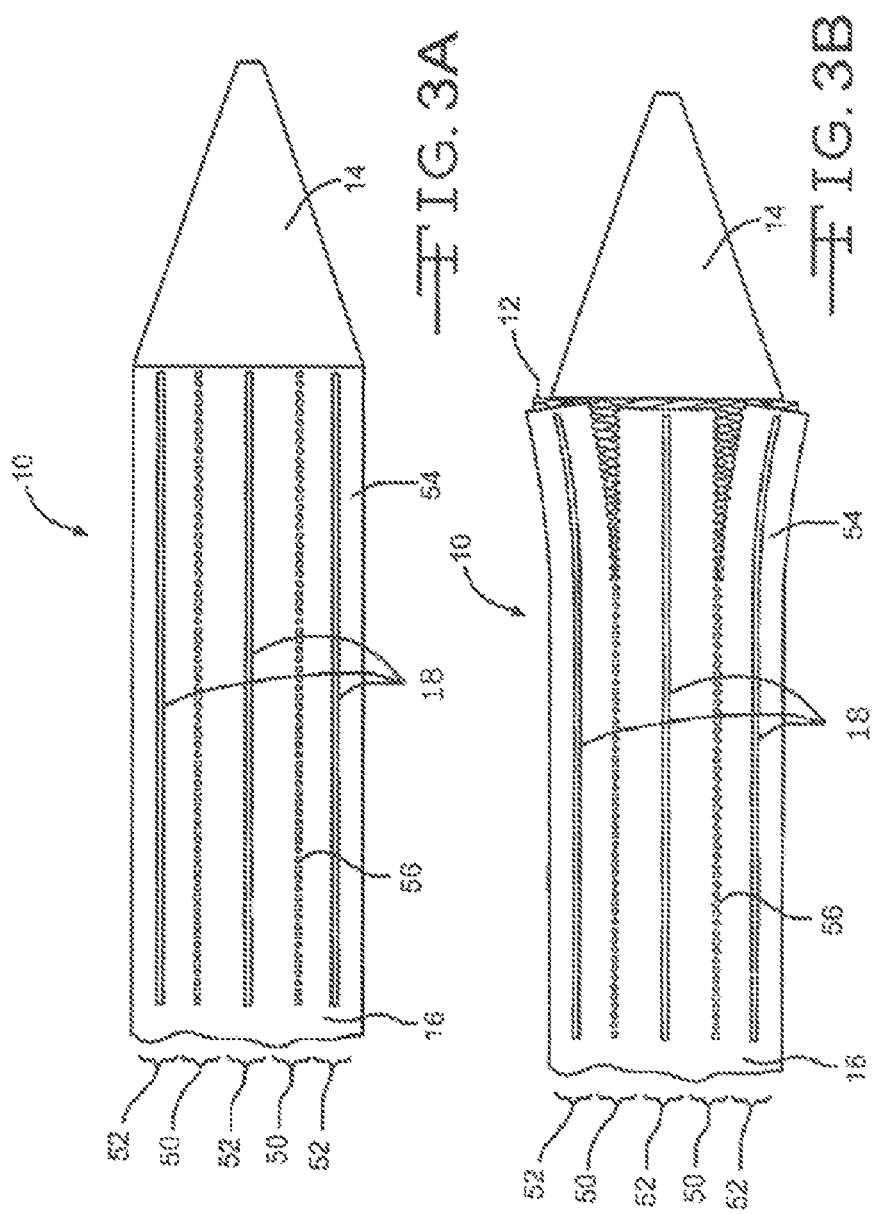

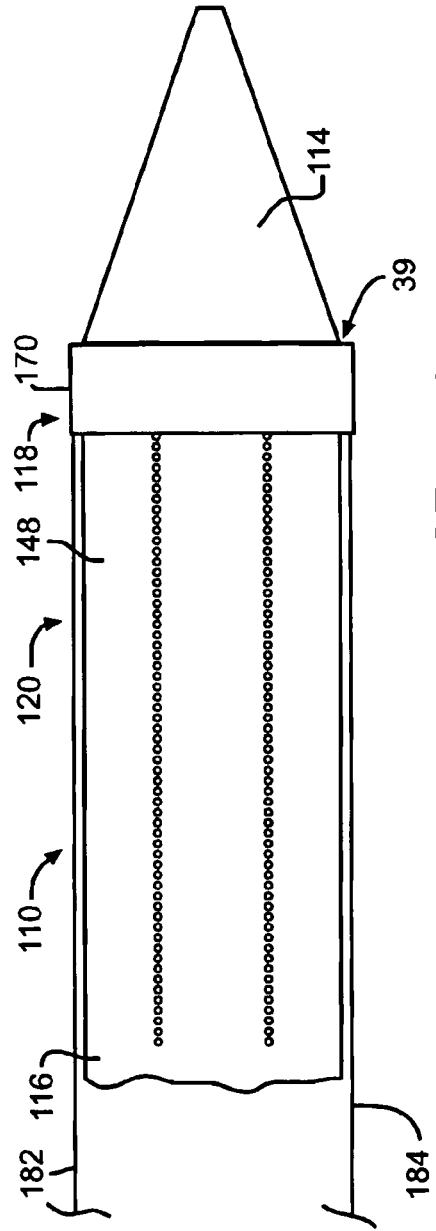
FIG. 4
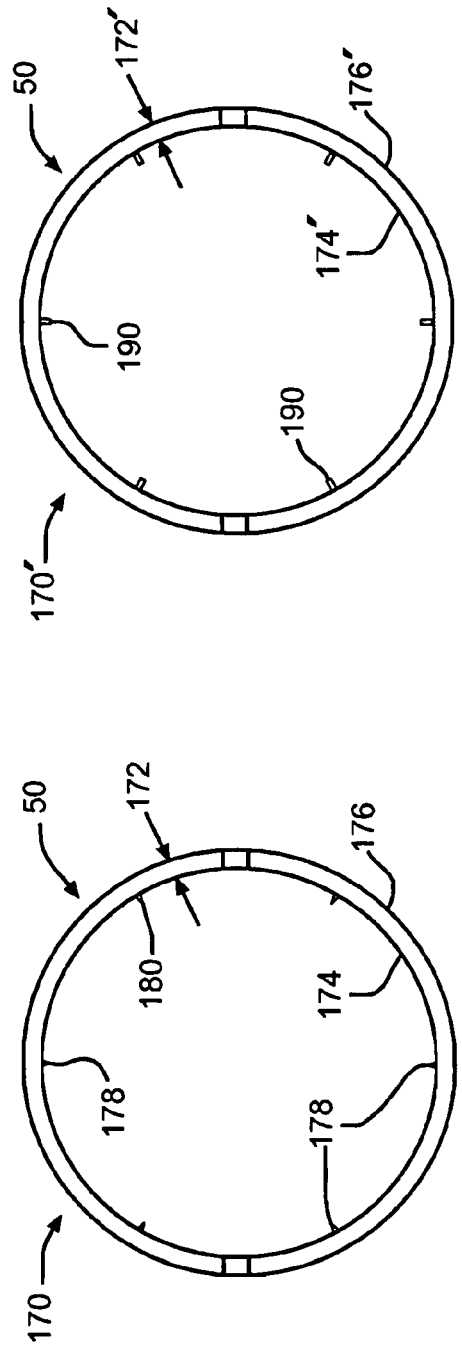
FIG. 5
FIG. 6

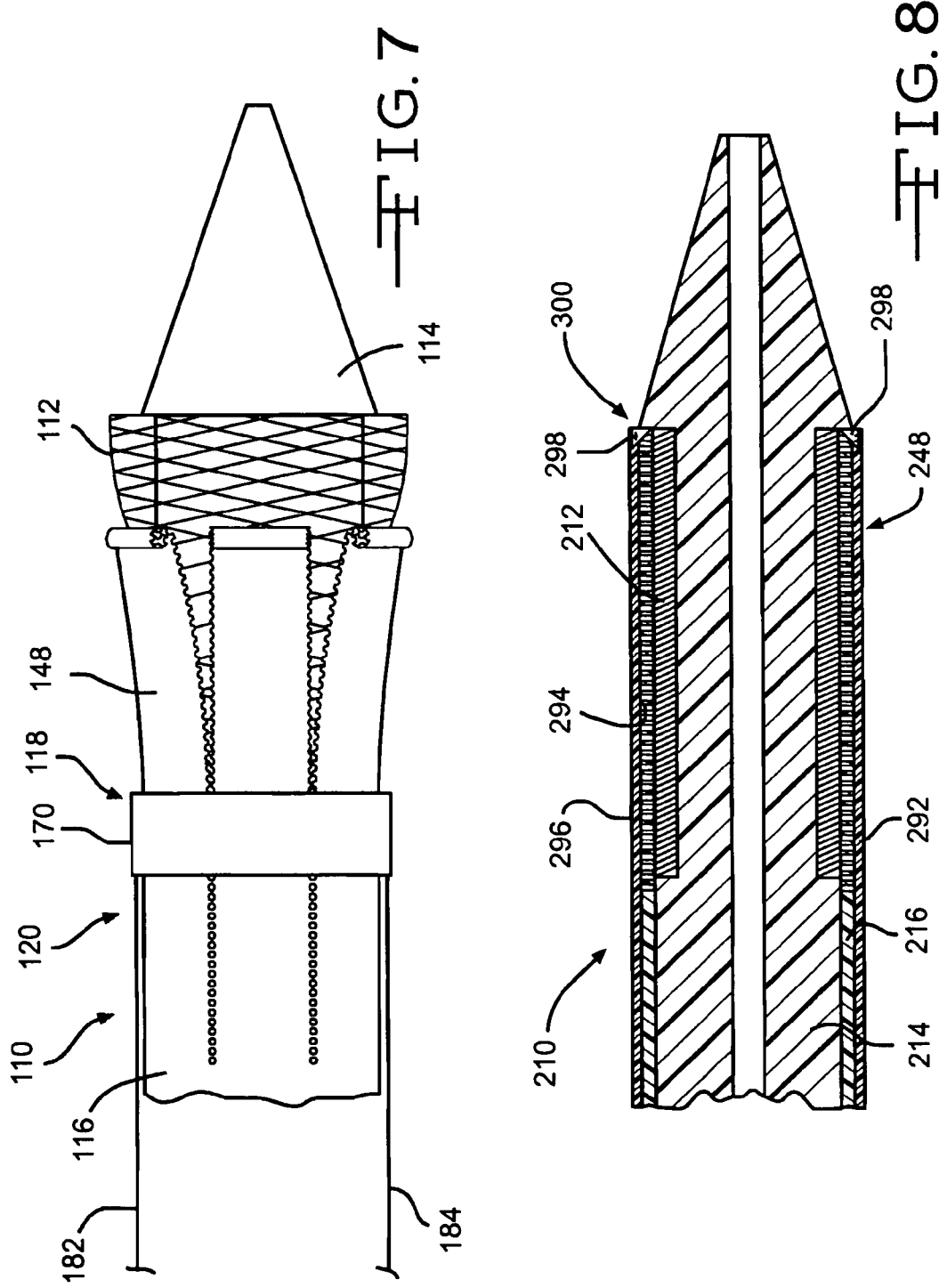

MEDICAL DEVICE DELIVERY SYSTEM WITH SHEATH SEPARATION

CROSS-REFERENCE TO RELATED APPLICATION

This application claims priority to U.S. Provisional Application No. 60/909,450, filed on Mar. 31, 2007, the entire contents of which are hereby incorporated by reference into this disclosure.

FIELD

Apparatuses, systems, and methods for implantation of an intraluminal medical device in a body vessel are described. The invention can be applied in various fields of medicine.

BACKGROUND

A variety of expandable intraluminal medical devices have been developed over recent years. For example, stents are routinely used in several body lumens as a means for providing support to ailing vessels, such as coronary and non-coronary vessels. Occlusion devices are used to substantially block fluid flow through a body vessel, and prosthetic valves are used to regulate fluid flow through a body vessel. Both prosthetic heart valves and venous valves have been the subject of significant development efforts in recent years.

Expandable intraluminal medical devices are typically delivered to a point of treatment using a delivery system designed for percutaneous techniques. In a conventional delivery procedure, a caregiver navigates the delivery system through one or more body vessels until the expandable intraluminal medical device, which is typically contained in a distal tip of the delivery system, is positioned at or near the desired point of treatment. Next, the caregiver deploys the expandable intraluminal medical device from the delivery system, either by removing a constraining force for self-expandable devices or by providing an expansive force for balloon-expandable devices. Once deployment is complete, the delivery system is removed from the body vessel, leaving the intraluminal medical device in an expanded configuration at the point of treatment. This delivery and deployment technique is largely conventional and is used for most types of expandable intraluminal medical devices, including stents, occluders, valves, and other types of devices.

During delivery, expandable intraluminal medical devices are maintained in a compressed or reduced-diameter configuration within the delivery system to ensure navigability of the delivery system through the body vessel. Generally, delivery systems for implanting expandable intraluminal medical devices in body vessels include a sheath placed over a dilator or other elongated member. The expandable intraluminal medical device is disposed on the dilator, between its outer surface and the inner surface of the sheath. The sheath provides the constraining force that maintains self-expandable intraluminal medical devices in the compressed configuration. Following navigation of the delivery system to a point of treatment in a body vessel, the sheath and/or dilator are moved relative to each other to remove the constraining force of the sheath, allowing the intraluminal medical device to deploy. Self-expandable devices transition to the expanded configuration simply by removal of the constraining force, which other types of expandable intraluminal medical devices, such as balloon expandable devices, require the application of an outwardly-directed radial force, such as by inflation of an underlying balloon, to achieve their expanded configuration.

The relative movement between the sheath and dilator during deployment results in friction between the interior surface of the sheath and the exterior surface of the intraluminal medical device. Extensive friction can be disadvantageous for a variety of reasons. For example, it may cause the intraluminal medical device to move relative to the dilator as the sheath or dilator is moved, which may result in deployment of the intraluminal medical device at a point that is spaced from the intended point of treatment. Even a slight spacing from the intended point of treatment can be disadvantageous for certain types of expandable intraluminal medical devices and/or certain clinical situations, such as deployment of stents at a plaque site within a body vessel, deployment of a valve at a desired valving location, and deployment of a stent-graft device at a desired exclusion site in a body vessel. The friction between the interior surface of the sheath and the exterior surface of the intraluminal medical device also creates the possibility for damage to the intraluminal medical device. For example, several intraluminal medical devices include a graft member or other attached component. Friction between the sheath and the underlying device may increase the likelihood that the graft will crease, tear, or even detach from the associated support frame during deployment. Furthermore, such friction could disrupt localized bioactive deposits that are associated with the support frame, graft, or other attached member, such as localized deposits of a therapeutic that are intended for contact with a specific portion of the body vessel wall.

Thus, there is a need for medical device delivery systems that provide advantageous frictional properties between the sheath and the underlying expandable intraluminal medical device during deployment of the medical device at a point of treatment in a body vessel.

BRIEF SUMMARY OF EXEMPLARY EMBODIMENTS

Medical device delivery systems are provided. A delivery system according to one exemplary embodiment comprises an elongated body adapted for insertion into a body vessel; an intraluminal medical device disposed on the distal end of the elongated body and adapted for deployment within the body vessel; a tubular member disposed around the intraluminal medical device such that the intraluminal medical device is constricted between the tubular member and the elongated body; and means for separating the second distal end of the tubular member into two or more portions.

Various structures can be used as the means for separating the second distal end of the tubular member into two or more portions. In one exemplary embodiment, the means for separating comprises an annulus disposed around the distal end of the tubular member and having one or more cutting edge. In another exemplary embodiment, the means for separating comprises one or more strips of shape memory materials attached to the distal end of the tubular member and adapted to adopt a configuration that facilitates separation of two or more portions of the distal end upon activation, such as upon achieving a particular temperature.

In exemplary embodiments, the distal end of the tubular member includes one or more structural or material properties that facilitate the separation of the distal end into two or more portions. For example, the distal end of the tubular member can include first and second sections having different structural integrities. The section with the lower structural integrity can be separated, such as by cutting or splitting, by the means for separating. In exemplary embodiments, the distal end of the tubular member include one or more holes in the tubular member. One or more linear perforations can be included in the distal end of the tubular member. Also, the material of the distal end can be chemically manipulated to facilitate its separation into two or more sections by the means for separating. For example, the polymer units of the tubular member, in the section having a lower structural integrity, can be aligned in a manner that facilitate splitting.

A medical device delivery system according to another exemplary embodiment comprises an elongated body adapted for insertion into a body vessel; an intraluminal medical device disposed on the distal end of the elongated body and adapted for deployment within said body vessel; a tubular member disposed around the intraluminal medical device and having at least one linear plurality of holes in the distal end; and means for separating the distal end of the tubular member into two or more portions across the line formed by the linear plurality of holes.

Methods of deploying intraluminal medical devices in a body vessel are also provided. An exemplary method comprises the steps of introducing a delivery system according to an embodiment of the invention into a body vessel; navigating the delivery system through the body vessel to a desired point of treatment; separating at least two portions of the distal end of the tubular member of the delivery system; deploying the intraluminal medical device at the desired point of treatment; and withdrawing the delivery system from the body vessel, leaving the deployed intraluminal medical device at the point of treatment.

Additional understanding of the invention can be obtained with review of the following detailed description of exemplary embodiments and the appended drawings, which illustrate the described exemplary embodiments.

BRIEF DESCRIPTION OF THE DRAWINGS

The following appended drawings illustrate exemplary embodiments of the invention and are not considered to limit the scope of the invention or its protection.

FIG. 3A is an elevational view of the distal end of the delivery system illustrated in FIG. 1. Separation members are in a first, unactivated position.

FIG. 3B is an elevational view of the distal end of the delivery system illustrated in FIG. 1. Separation members are in a second, activated position.

FIG. 4 is an elevational view of the distal end of a delivery system according to a second exemplary embodiment. A separation annulus is in a first, unactivated position.

FIG. 5 is an end view of a separation annulus for use with the delivery system illustrated in FIG. 4.

FIG. 6 is an end view of an alternative separation annulus.

FIG. 7 is an elevational view of the distal end of the delivery system according to the second exemplary embodiment. A separation annulus is in a second, activated position.

FIG. 8 is a sectional view of the distal end of a delivery system according to a third exemplary embodiment.

DETAILED DESCRIPTION OF EXEMPLARY EMBODIMENTS

Figure 1:
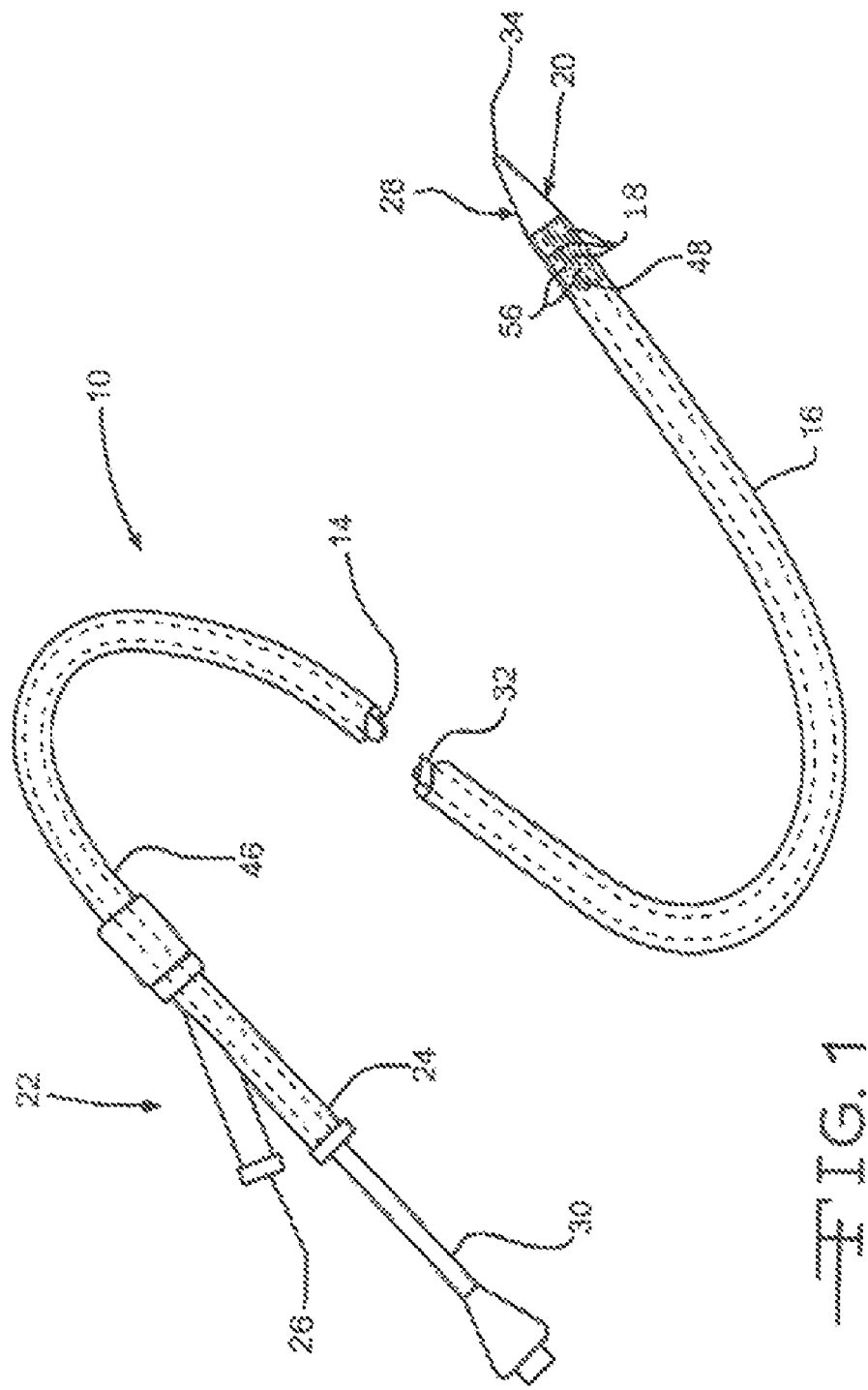
FIG. 1 is a perspective view of a delivery system according to a first exemplary embodiment.

The following detailed description and the appended drawings describe and illustrate exemplary embodiments of the invention solely for the purpose of enabling one of ordinary skill in the relevant art to make and use a delivery system according to the invention. As such, the description and illustration of the embodiments are purely exemplary in nature and are in no way intended to limit the scope of the invention, or its protection, in any manner.

FIGS. 1, 2, and 3A through 3C illustrate a delivery system 10 according to a first exemplary embodiment. The delivery system 10, and all delivery systems according to the invention, are useful for implanting one or more intraluminal medical device(s) 12, such as stents, stent grafts, occluders, filters, and intraluminal valve devices, including venous valve and heart valve devices, and the like at a point of treatment in a body vessel of an animal, such as a human or other animal. Delivery systems according to embodiments of the invention are particularly well-suited for use with expandable intraluminal medical devices, including self-expandable and balloon-expandable stents and other devices including self-expandable and balloon-expandable support frames.

The delivery system 10 includes the intraluminal medical device 12, an elongated member 14, such as a conventional delivery system dilator known in the art, a tubular member 16, and means for separating 56 two or more portions of the tubular member 16. The intraluminal medical device 12 is disposed on and/or around the elongated body 14 and substantially under the tubular member 16 prior to deployment of the intraluminal medical device in a body vessel. The tubular member 16 is disposed over the elongated body 14 such that the intraluminal medical device 12 is disposed substantially between the tubular member 16 and at least a portion of the elongated body 14. Once the delivery system 10 is placed at a desired point of treatment in a body vessel, and as described more fully below, the means for separating 56 two or more portions of the tubular member 16 aids in deploying the intraluminal medical device 12 by separating two or more portions of the distal end of the tubular member 16 from each other. This separation enlarges the circumference of the distal end of the tubular member such that the coefficient of friction between the inner surface of the tubular member and the outer surface of the intraluminal medical device is less than that which would occur between the inner surface of the tubular member and the outer surface of the intraluminal medical device in the absence of such separation.

Figure 2:
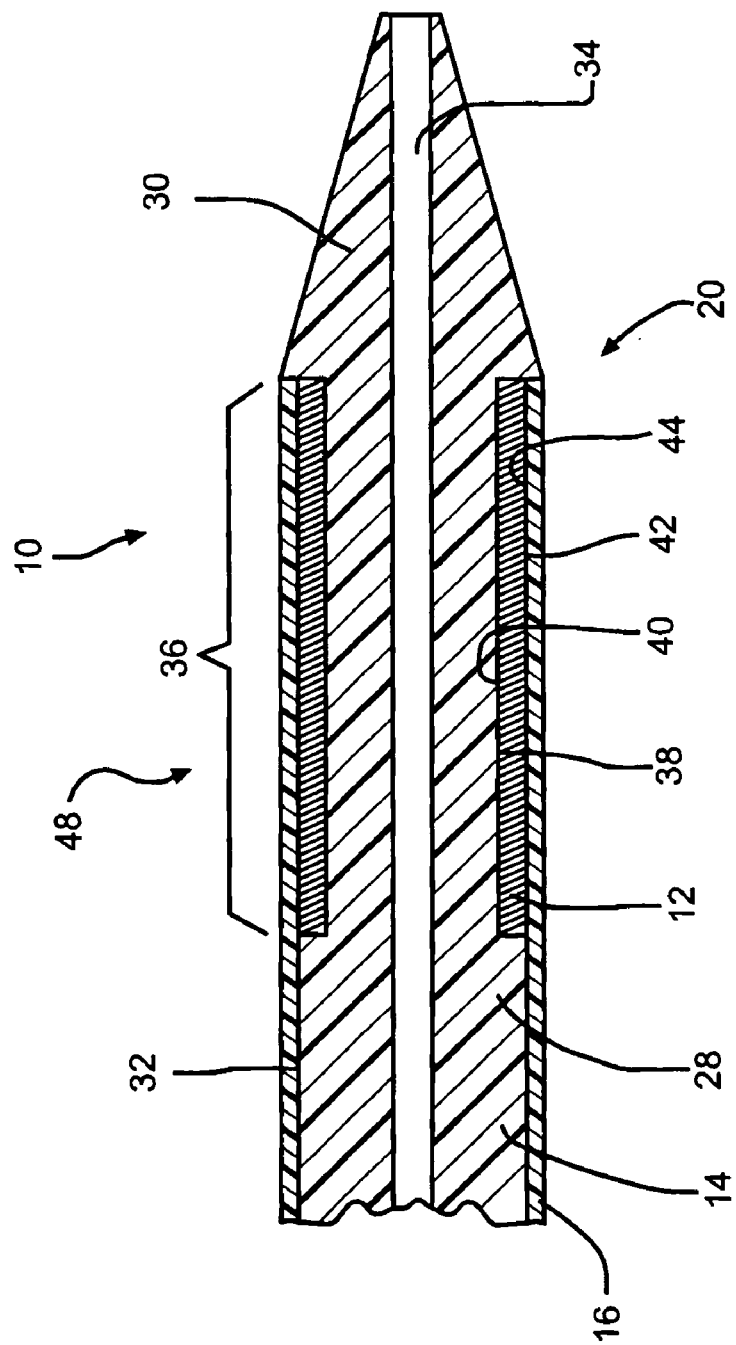
FIG. 2 is a sectional view of the distal end of the delivery system illustrated in FIG. 1.

The delivery system 10 includes a distal end 20 and a proximal end 22. The distal end 20 of the delivery system 10 is insertable into the body vessel and can include appropriate structural features for insertion, such as the tapered end on the elongated body 14 as illustrated in FIGS. 1 and 2. The proximal end 22 of the delivery system 10 may include a connector 24, a port 26, a combination thereof, or any other suitable components. For example, the proximal end 22 of the delivery system 10 may include a Touhy-Borst adapter.

The elongated body 14 of the delivery system 10 has a distal end 28, a proximal end 30, and an outer surface 32. As discussed above, the distal end 28 of the elongated body 14 may be tapered to aid in the insertion into and navigation of the delivery system 10 through the body vessel. The elongated body 14 defines a lumen 34 that extends between the distal end 28 and the proximal end 30. The lumen 34 is adapted to receive devices aiding in the introduction, positioning, and/or removal of the delivery system 10. For example, a wire guide (not shown) may be used to introduce and position the distal end 20 of the delivery system 10 at a desired point of treatment within the body vessel according to percutaneous placement techniques known in the art.

While the embodiment illustrated in FIG. 1 includes a lumen 34 extending the entire length of the elongated body 14, it is understood that an alternative lumen can be used. For example, a lumen that extends along only a portion of the length of the elongated body 14 may be used. Further, over-the-wire, rapid exchange, short wire, and intraductal exchange type delivery systems are all contemplated and considered to be within the scope of the invention.

FIG. 2 illustrates a sectional view of the distal end 20 of the delivery system 10. The intraluminal medical device 12 is disposed in a device chamber 36 defined by the distal end 28 of the elongated body 14. An exterior surface 38 of the device chamber 36 is adjacent to an inner surface 40 of the intraluminal medical device 12. An outer surface 42 of the intraluminal medical device 12 is adjacent to an inner surface 44 of the tubular member 16. It is noted that the elongated body 14 need not define an actual chamber and that the intraluminal medical device 12 could simply be disposed on and/or around the outer surface 32 of the elongated body 14.

The intraluminal medical device 12 may be any suitable intraluminal medical device, examples of which include a stent, a valve device, a filter, an occluder, a distal protection device, a stent graft, and the like. Further, the intraluminal medical device 12 can be a self-expandable device or a device that requires an input of force for expansion, such as a balloon-expandable device. The specific intraluminal medical device selected for the delivery system 10 according to a particular embodiment according to the invention will depend on several considerations, including the clinical conditions for which the delivery system 10 is being used. For example, suitable intraluminal medical devices for use in the delivery system 10 according to the invention may include those described in U.S. Pat. No. 6,200,336 to Pavcnik et al. for a MULTIPLE-SIDED INTRALUMINAL MEDICAL DEVICE; U.S. application for patent Ser. No. 10/642,372 of Pavcnik et al. for an IMPLANTABLE VASCULAR DEVICE, filed on Aug. 15, 2003; and U.S. application for patent Ser. No. 10/828,716 of Case, et al. for an ARTIFICAL VALVE PROSTHESIS WITH IMPROVED FLOW DYNAMICS, filed on Apr. 21, 2004; each of which is hereby incorporated by reference in its entirety for the purpose of describing suitable intraluminal medical devices.

The tubular member 16 includes a proximal end 46 and a distal end 48 and extends substantially along the entire length of the delivery system 10. Alternatively, the tubular member 16 could extend along only a portion of the length of the elongated body 14 and/or a portion of the length of the intraluminal medical device 12.

In the embodiment illustrated in FIGS. 1, 2 and 3A through 3C, the tubular member 16 of the delivery system 10 is disposed about the elongated body 14 with portions of the inner surface 44 of the tubular member adjacent the outer surface 32 of the elongated body 14 and other portions adjacent the outer surface 42 of the intraluminal medical device 12.

Figure 3C:
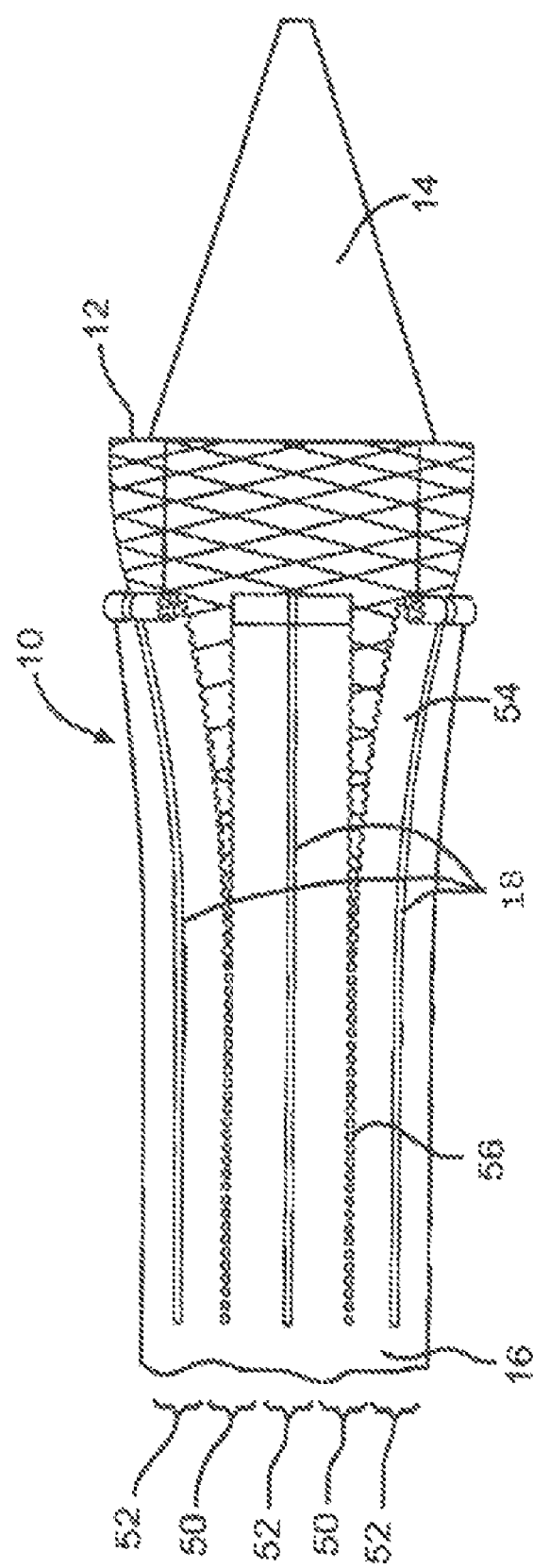
FIG. 3C is a sectional view of the distal end of the delivery system illustrated in FIG. 1. Separation members are in a third, coiled position.

As best illustrated in FIGS. 3A through 3C, the distal end 48 of the tubular member 16 in the delivery device 10 according to the first exemplary embodiment includes alternating first 50 and second 52 sections, an inner surface 44, and an outer surface 54. The first section 50 of the tubular member 16 includes an area having lower structural integrity in comparison to the second section 52 of the tubular member 16. As used herein, the term "lower structural integrity" refers to a property of a section of the tubular member that requires less separation force to separate adjacent portions than the separation force required to separate portions adjacent a section having a relatively greater structural.

The area of the first section 50 having lower structural integrity can be formed in any suitable manner and can have any suitable structure. For example, as best illustrated in FIG. 3A, the first section 50 can include a hole or series of holes bored through or otherwise established in the tubular member 16 to form a perforation in the distal end of the tubular member 16. Also, a series of bubbles or other chambers can be formed in the tubular member, preferably in a line formation similar to the perforation illustrated in FIG. 3A. In alternative embodiments, the chemistry of the distal end of the tubular member 16 can be manipulate to allow the first section to have a lower structural integrity than that of the second section. For example, the polymer units can be aligned in the first section in a manner that facilitates directed cracking upon application of a force to the distal end of the tubular member 16. In this embodiment, the first section has an outward appearance that is substantially similar to the second section despite its lower structural integrity.

The first section 50 may be formed on the tubular member 16 during the initial manufacturing process such as, for example, through the process of injection molding. Alternatively, the first section 50 of the tubular member 16 may be created by manipulating the tubular member 16 such as, for example, through scoring the inner surface 44 and/or outer surface 54 of the tubular member 16. It should be noted that any suitable structure and/or process for creating the lower structural integrity in the first section 50 may be used to provide the desired lowered structural integrity of the first section 50 in comparison to the second section 52.

The tubular member 16 and all components of the delivery system 10 can be formed of any suitable material, including conventional materials biocompatible plastics used in medical device delivery systems. Other suitable materials for the tubular member 16 include biocompatible metals. A skilled artisan will be able to select a suitable material or materials for use in the tubular member 16 and other components of the delivery system 10 based on the suitability of the material for use in clinical applications, the physiological environment within which the delivery system 10 is intended to be used, and other appropriate considerations.

In the embodiment illustrated in FIGS. 1, 2, and 3A through 3C, the means for separating 56 the tubular member 16 into two or more portions comprises one or more strips 18 of a shape memory material, such as a nickel-titanium alloy, a ferromagnetic shape memory alloy, and the like. In the illustrated embodiment, the strips 18 are attached to the outer surface 54 of the tubular member 16, such as by adhesion or another suitable attachment. The strips 18 are substantially flush with the tubular member 16 such that during insertion and placement of the delivery system 10, the strips 18 do not substantially impede the movement of the delivery system 10 through the body vessel. A skilled artisan will be able to determine appropriate dimensions for the strips 18, including length, width, and thickness, based on various considerations, including the length of the intraluminal medical device 12, the actual or expected inner diameter of the body vessel within which the intraluminal medical device 12 is intended to be deployed, and the shape memory abilities and properties of the selected material. Furthermore, a skilled artisan will be able to determine an appropriate number and arrangement of strips 18 for inclusion in a particular delivery system according to a specific embodiment of the invention based on various considerations, including the amount of force required to separate portions of the distal end 20 of the delivery system 10. While FIGS. 3A through 3C illustrate the strips 18 spaced substantially equidistant from each other around the circumference of the distal end 20 of the tubular member 16, any suitable arrangement can be used.

Although the strips 18 are positioned on the outer surface 54 of the tubular member 16 in FIGS. 3A through 3C, the strips 18 may be placed on the inner surface 44 of the tubular member 16 such that the strips 18 are in contact with the outer surface 42 of the intraluminal medical device 12 during insertion and/or placement. Also alternatively, the strips 18 may be embedded within the thickness of the tubular member 16.

FIGS. 3A through 3C illustrate the distal end 20 of the delivery system 10 according to a first exemplary embodiment with the means for separating 56 the distal end 20 of the tubular member 16 into two or more portions at various stages of activation. In FIG. 3A, the strips 18 are in a first, unactivated position. In this position, each of the strips 18 has an axis that is substantially parallel to a lengthwise axis of the distal end 20 of the delivery system 10. This shape memory material is advantageously trained to adopt this first, unactivated position when the strips 18 are at room temperature. FIG. 3B illustrates the strips 18 in a second, activated position in which each of the strips 18 has started to adopt a second configuration, such as a coiled configuration the shape memory material has been trained to adopt at a second temperature, such as body temperature. The activation of the strips 18 begins to occur once the activation temperature is achieved and causes a separation to occur in the distal end 20 of the tubular member 16 at the first portion 50 and its area of lower structural integrity. For example, as illustrated in FIG. 3B, the activation of the strips 18 has forced separation of the distal end 20 of the tubular member 16 along the perforation within the first area 50.

The strips 18 exert a separation force on the tubular member 16 when moving from the first unactivated position as illustrated in FIG. 3A to the second activated position illustrated in FIG. 3B such that the tubular member 16 separates into one or more portions. Although the separation of the tubular member 16 is aided by the lower structural integrity of the first section 50 of the tubular member 16, it should be appreciated that the tubular member 16 need not have varying degrees of structural integrity, (e.g. the first section 50 and the second section 52), if the separation force exerted by the strips 18 can alone separate the tubular member 16 into one or more portions. For example, by increasing the number of strips 18 placed on and/or within the tubular member 16 the separation force may be increased causing the tubular member 16 to separate upon activation of the shape-memory material in the strips 18.

If the body vessel provides sufficient clearance and the strips 18 have been trained to do so, a coiled configuration can be adopted as illustrated in FIG. 3C. Use of a coiled configuration is considered advantageous at least because it may provide for deployment of the intraluminal medical device 12 from the delivery system substantially in the absence of friction between the inner surface 44 of the tubular member 16 and the outer surface 42 of the intraluminal medical device. That is, if the strips 18 are able to coil back to completely reveal the intraluminal medical device 12 during deployment, little or no relative movement between the tubular member 16 and the elongated body 14 and medical device 12 would need to occur, essentially eliminating this friction. It is noted, though, that achievement of the full coiled configuration in which the strips 18 are sufficiently coiled back to fully reveal the intraluminal medical device 12 may be difficult to achieve due to size constraints within the body vessel. The initial activation of the strips 18, illustrated in FIG. 3B and described above, is considered sufficient if it achieves the desired separation of the portions of the distal end 20 of the tubular member 16.

While activation of the strips 18 is described above in relation to a temperature change, it is noted that other suitable activation processes can be used based on the properties of the shape memory material selected for inclusion in the strips 18. For example, activation may occur through modification of the magnetic field for ferromagnetic strips, pressure modification, or the like depending on the specific type of shape-memory material used.

FIG. 4 illustrates a delivery system 110 according to a second exemplary embodiment. The delivery system 110 according to this embodiment is similar to the embodiment described above and illustrated in FIGS. 1, 2, and 3A through 3C, except as detailed below. Thus, the delivery system 110 includes an intraluminal medical device 112, an elongated body 114, a tubular member 116, and a means for separating 118 two or more portions of the distal end 120 of the tubular member 116. In this embodiment, the means for separating 118 comprises a separation annulus 170 having one or more blades adapted to cut the distal end 120 of the tubular member 116 at the area having a lower structural integrity. The separation annulus 170 is disposed on the outer surface 154 of the tubular member and has a thickness 172 that is advantageous dimensioned to minimize the additional thickness added to the overall radius of the delivery system 10 such that the separation annulus 170 does not substantially impede the movement of the delivery system 110 through the body vessel during navigation. The separation annulus 170 is advantageously substantially flush with the outer surface 154 of the tubular member.

Wire members 182, 184 are attached to the separation annulus 170 and extend along the length of the delivery system 110 to a proximal point that allows a user to grasp and pull the wires during use of the delivery system 110. The proximal end of each wire member 182, 184 remains accessible to a user outside of the body vessel while the distal end is attached to the separation annulus 170 in any suitable fashion, such as adhesion, spot welds, knotting, and the like. While the wire members 182, 184 are illustrated adjacent the tubular member 116, it is understood that the wire members 182, 184 can be passed through one or more accessory lumens or channels defined by the tubular member 116, so long as the lumen or channel allows for retraction of the members 182, 184 and the attached separation annulus 170 as described below.

FIG. 5 illustrates the separation annulus 170 included in the delivery system 110 illustrated in FIG. 4. In this embodiment, the separation annulus 170 includes an inner surface 174, an outer surface 176, and one or more blades 178. The blades(s) 178 are adjacent, integral, or attached to the inner surface 174 of the separation annulus 170. Each blade 178 has a cutting edge or point 180 adapted to separate portions of the distal end 148 of the tubular member 116 when the separation annulus 170 is moved proximally along the length of the tubular member 116. The cutting edge or point 180 may be placed in a pre-fabricated depression or indentation (not shown) on the tubular member 116 illustrated in FIG. 4 during insertion and placement of the delivery system 110, although this is not required.

FIG. 6 illustrates an alternative separation annulus 170'. In this embodiment, one or more pins 190 project radially from an inner surface 174'. The pins 190 of the separation annulus 170' may be placed in a prefabricated depression or indentation (not shown) on the tubular member 116 illustrated in FIG. 4 during insertion and placement of the delivery system 110, although this is not required.

To initiate separation of the portions of the distal end 148 of the tubular member 116, a user retracts the wire member 182, 184 by pulling on the members while maintaining the tubular member 116 in a substantially fixed position. As a result of this retraction, the separation annulus 170 is moved proximally along the tubular member 116 which, in turn, causes separation of portions of the distal end 148 of the tubular member 116 by interaction between the blade(s) 178 and the tubular member 116. Retraction of the wire members 182, 184 can be stopped once a desired amount of separation of portions in the distal end 148 of the tubular member has been achieved. For example, once the wire members 182, 184 have been retracted by a length that is substantially equal to between about one-half and one and one half times the length of the intraluminal medical device 112, further retraction of the wire members 182, 184—and further separation of portions of the distal end 148 of the tubular member by resulting movement of the separation annulus 170—may be unnecessary. A retraction length that is substantially equal to about the length of the intraluminal medical device is considered sufficient and particularly advantageous.

While the wire members 182, 184 are described as 'wire' members, it is expressly contemplated that any suitable material can be used in the members 182, 184. The members 182, 184 need only be biocompatible or capable of being rendered biocompatible, and be capable of retracting the attached separation annulus 170 upon application of a suitable retraction force to their proximal ends. Furthermore, while two members 182, 184 are described and illustrated in connection with this embodiment, it is expressly contemplated that any suitable number and configuration can be used. A skilled artisan will be able to select an appropriate material, number and configuration for the members 182, 184 in a specific delivery system according to a particular embodiment based on various considerations, including the nature and size of the vessel within which the delivery system is intended to be used.

FIG. 8 illustrates a delivery system 210 according to a second exemplary embodiment. The delivery system 210 according to this embodiment is similar to the embodiment described above and illustrated in FIGS. 4 and 7, except as detailed below. Thus, the delivery system 210 includes an intraluminal medical device 212, an elongated body 214, a tubular member 216, and a means for separating two or more portions of the distal end 248 of the tubular member 216. In this embodiment, the means for separating comprises an elongated outer tube 292 having an inner surface 294, an outer surface 296, and one or more cutting edges 298 disposed on the inner surface 294.

The inner surface 294 of the elongated outer tube 292 is adjacent to the inner surface 242 of the tubular member 216. The elongated outer tube 292 further comprises a distal end 300 and a proximal end (not shown) and advantageously extends along substantially the entire length of tubular member 216. The proximal end (not shown) of the elongated outer tube 292 remains accessible to the user outside of the body vessel during use of the delivery system 210. During use of the delivery system 210 according to this embodiment, a user retracts the elongated outer tube 292 while maintaining the tubular member 216 in a substantially fixed position such that the cutting edge(s) 298 move proximally along the outer tube 216 such that the distal end 248 of the outer tube 216 separates into two or more portions.

The cutting edge(s) 298 advantageously comprise a blade having a cutting surface suitable for cutting the material of the distal end of the tubular member 216.

Figure 9:
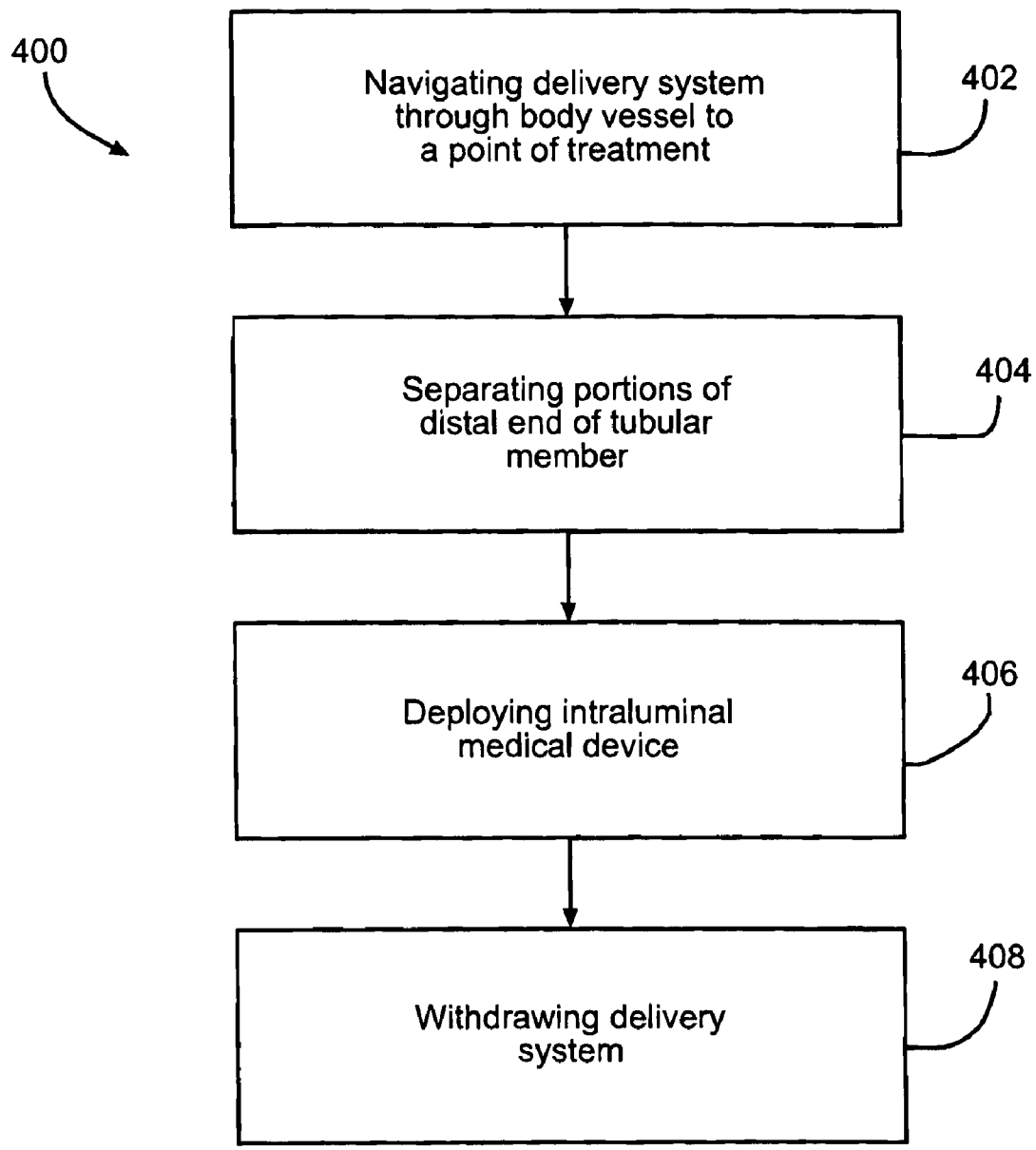
FIG. 9 is a flow chart representing an exemplary method of deploying an intraluminal medical device.

FIG. 9 illustrates an exemplary method of deploying an intraluminal medical device according to the invention. The order of the steps in FIG. 9 is exemplary in nature and is not necessary or critical. An initial step 400 comprises introducing a delivery system according to an embodiment of the invention into a body vessel. Another step 402 comprises navigating the delivery system through the body vessel to a desired point of treatment. Another step 404 comprises separating at least two portions of the distal end of the tubular member, such as by activating a suitable means for separating, as described above. Examples of suitable separating steps include initiating a configuration change in one or more shape memory members associated with the tubular member and cutting the tubular member at one or more locations.

Another step 406 comprises deploying the intraluminal medical device at the desired point of treatment. For self-expandable intraluminal medical devices, this can occur as a result of the step 404 of separating at least two portions of the distal end of the tubular member. Alternatively, for balloon-expandable and other suitable intraluminal medical devices, this step can be achieved by applying an appropriate expansion force onto the intraluminal medical device, such as by inflation of an underlying balloon. Another step 408 comprises withdrawing the delivery system from the body vessel, leaving the deployed intraluminal medical device at the point of treatment.

The embodiments described and illustrated herein are exemplary in nature and, as such, are not intended to limit the scope of the invention or its protection in any manner. Rather, they serve only to aid skilled artisans in making and using medical device delivery systems in accordance with the invention.

What is claimed is:

1. A medical device delivery system, comprising:
   an elongated body adapted for insertion into a body vessel, the elongated body having first proximal and first distal ends;
   an intraluminal medical device disposed on the first distal end of the elongated body and adapted for deployment within said body vessel;
   a tubular member having two or more portions and having second distal and second proximal ends, the second distal end disposed around the intraluminal medical device such that the intraluminal medical device is constricted between the second distal end of the tubular member and the first distal end of the elongated body, the tubular member formed of a first material;
   a strip of shape memory material contacting at least one of the two or more portions and adapted to adopt a coiled configuration, the shape memory material different from the first material; and
   an annulus disposed around the second distal end of the tubular member, the annulus having an inner surface disposed adjacent the second distal end of the tubular member and at least one cutting edge disposed on the inner surface, the cutting edge adapted to separate the two or more portions of the second distal end of the tubular member.

2. The medical device delivery system of claim 1, wherein the at least one cutting edge comprises a plurality of cutting edges.

3. The medical device delivery system of claim 2, wherein the cutting edges of the plurality of cutting edges are spaced equidistantly about a circumference of the annulus.

4. The medical device delivery system of claim 1 further comprising at least one wire member attached to the annulus and extending along substantially the entire length of the tubular member.

5. The medical device delivery system of claim 1, wherein the second distal end of the tubular member comprises first and second sections having different structural integrities.

6. The medical device delivery system of claim 5, wherein the first section comprises at least one hole in the tubular member.

7. The medical device delivery system of claim 5, wherein the first section comprises a plurality of holes in the tubular member.

8. The medical device delivery system of claim 7, wherein the plurality of holes is substantially arranged in a straight line.

9. The medical device delivery system of claim 1, wherein the second distal end of the tubular member comprises a first set of sections and a second set of sections, and wherein each of the first set of sections has a different structural integrity than each of the second set of sections.

10. The medical device delivery system of claim 9, wherein each of the first set of sections comprises at least one hole in the tubular member.

11. The medical device delivery system of claim 9, wherein each of the first set of sections comprises a plurality of holes in the tubular member.

12. The medical device delivery system of claim 11, wherein the first and second sets of sections are disposed around a circumference of the second distal end of the tubular member in an alternating pattern.

13. The medical device delivery system of claim 1, wherein the intraluminal medical device comprises a self-expandable intraluminal medical device.

14. The medical device delivery system of claim 1, wherein the intraluminal medical device comprises a self-expandable stent.

15. The medical device delivery system of claim 1, wherein the intraluminal medical device is adapted to expand upon the input of a force.

16. The medical device delivery system of claim 15, wherein the intraluminal medical device comprises a balloon-expandable intraluminal medical device.

17. A medical device delivery system, comprising:
- an elongated body adapted for insertion into a body vessel, the elongated body having first proximal and first distal ends;
- an intraluminal medical device disposed on the first distal end of the elongated body and adapted for deployment within said body vessel;
- a tubular member having two or more portions and having a second distal end disposed around the intraluminal medical device, the second distal end comprising at least one plurality of holes in the tubular member substantially arranged in a line, the tubular member formed of a first material;
- a strip of shape memory material contacting at least one of the two or more portions and adapted to adopt a coiled configuration, the shape memory material different from the first material; and
- one or more cutting edges disposed adjacent the at least one plurality of holes in the tubular member and adapted to be retracted along the at least one plurality of holes in the tubular member to separate portions of the tubular member.

18. The medical device delivery system of claim 17, wherein the intraluminal medical device comprises a self-expandable intraluminal medical device.

19. The medical device delivery system of claim 17, wherein the intraluminal medical device is adapted to expand upon the input of a force.

20. A medical device delivery system, comprising:
- an elongated body adapted for insertion into a body vessel, the elongated body having first proximal and first distal ends;
- a self-expandable intraluminal medical device disposed on the first distal end of the elongated body and adapted for deployment within said body vessel;
- a tubular member having two or more portions and having a second distal end disposed around the self-expandable intraluminal medical device, the second distal end comprising a first set of sections and a second set of sections, each section of the first set of sections comprising a plurality of holes in the tubular member and having a different structural integrity than each section of the second set of sections, the tubular member formed of a first material;
- a strip of shape memory material contacting at least one of the two or more portions and adapted to adopt a coiled configuration, the shape memory material different from the first material;
- an annulus disposed around the second distal end of the tubular member, the annulus having an inner surface disposed adjacent the second distal end of the tubular member and at least one cutting edge disposed on the inner surface and adjacent one section of the first set of sections, the at least one cutting edge adapted to separate the two or more portions of the distal end of the tubular member; and
- at least one wire member attached to the annulus and extending along substantially the entire length of the tubular member, the at least one wire member adapted to retract the annulus along the second distal end of the tubular member to separate the two or more portions of the tubular member.

\* \* \* \* \*